(12) United States Patent
Hofmann et al.

(10) Patent No.: US 10,111,293 B2
(45) Date of Patent: Oct. 23, 2018

(54) METHOD OF ILLUMINATION HAVING LIGHT EMITTING DEVICE WITH CERAMIC CONVERSION MATERIAL

(71) Applicant: PHILIPS LIGHTING HOLDING B.V., Eindhoven (NL)

(72) Inventors: Bernd Hofmann, Aachen (DE); Hans-Helmut Bechtel, Roetgen (DE)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 618 days.

(21) Appl. No.: 14/074,938

(22) Filed: Nov. 8, 2013

(65) Prior Publication Data

US 2014/0062336 A1  Mar. 6, 2014

Related U.S. Application Data

(62) Division of application No. 12/298,047, filed as application No. PCT/IB2007/051352 on Apr. 16, 2007.

(30) Foreign Application Priority Data

Apr. 26, 2006  (EP) .................................. 06113294

(51) Int. Cl.
*F21V 9/08* (2018.01)
*H05B 33/08* (2006.01)
(Continued)

(52) U.S. Cl.
CPC ...... *H05B 33/0857* (2013.01); *A61B 1/00117* (2013.01); *A61B 1/0653* (2013.01); *A61B 1/0669* (2013.01); *A61B 1/0684* (2013.01); *A61N 5/0601* (2013.01); *A61N 5/062* (2013.01); *G02B 6/0003* (2013.01); *G02B 6/0006* (2013.01); *A61N 5/0603* (2013.01); *A61N 2005/0652* (2013.01); *A61N 2005/0662* (2013.01)

(58) Field of Classification Search
CPC ..... F21V 9/06; F21V 9/08; F21V 9/10; F21V 9/16; F21K 2/00
See application file for complete search history.

(56) References Cited

U.S. PATENT DOCUMENTS 5,128,846 A  7/1992  Mills et al.
5,721,795 A *  2/1998  Pelka .................. G02B 6/2817
385/12

(Continued)

FOREIGN PATENT DOCUMENTS

EP  1787571 A1  5/2007
JP  2003019112 A  1/2003
(Continued)

*Primary Examiner* — Ismael Negron
(74) *Attorney, Agent, or Firm* — Akarsh P. Belagodu

(57) ABSTRACT

A method of delivering light from a lighting device including having at least one main LED, at least one auxiliary LED, and at least one ceramic light conversion element placed longitudinal to the path of light emitted from the main LED and orthogonal to the auxiliary LED; the method including the steps of switching on the at least one main LED, and changing the color temperature of the light emitted from the lighting device by switching on the at least one auxiliary LED.

16 Claims, 4 Drawing Sheets

(51) Int. Cl.
  *A61B 1/00*    (2006.01)
  *A61B 1/06*    (2006.01)
  *A61N 5/06*    (2006.01)
  *F21V 8/00*    (2006.01)

(56) References Cited

U.S. PATENT DOCUMENTS

| | | | |
|---|---|---|---|
| 5,813,753 | A | 9/1998 | Vriens et al. |
| 6,273,589 | B1 * | 8/2001 | Weber .................. H01L 25/0753 |
| | | | 257/E25.02 |
| 6,350,041 | B1 * | 2/2002 | Tarsa ........................ F21K 9/00 |
| | | | 257/E33.072 |
| 6,466,135 | B1 | 10/2002 | Srivastava et al. |
| 6,630,691 | B1 * | 10/2003 | Mueller-Mach ........ H01L 33/08 |
| | | | 257/103 |
| 6,982,522 | B2 | 1/2006 | Omoto |
| 7,157,745 | B2 | 1/2007 | Blonder et al. |
| 7,196,354 | B1 | 3/2007 | Erchak et al. |
| 7,235,792 | B2 | 6/2007 | Elofson |
| 7,316,497 | B2 * | 1/2008 | Rutherford .......... H04N 9/3197 |
| | | | 348/E9.027 |
| 7,361,938 | B2 * | 4/2008 | Mueller .................. C04B 35/44 |
| | | | 257/79 |
| 7,514,721 | B2 * | 4/2009 | Krames .................. C04B 35/44 |
| | | | 257/103 |
| 7,777,243 | B2 | 8/2010 | Lin et al. |
| 7,837,348 | B2 * | 11/2010 | Narendran ................ F21K 9/00 |
| | | | 362/231 |
| 7,902,566 | B2 * | 3/2011 | Paolini .................... H01L 33/50 |
| | | | 257/88 |
| 8,684,555 | B2 * | 4/2014 | Hofmann ........... A61B 1/00117 |
| | | | 257/98 |
| 2001/0036083 | A1 | 11/2001 | Weber et al. |
| 2003/0007087 | A1 | 1/2003 | Hakamata et al. |
| 2003/0042493 | A1 | 3/2003 | Kazakevich |
| 2003/0044114 | A1 | 3/2003 | Pelka |
| 2003/0218880 | A1 | 11/2003 | Brukilacchio |
| 2004/0145308 | A1 | 7/2004 | Rossner et al. |
| 2004/0246744 | A1 | 12/2004 | Krupa et al. |
| 2005/0063197 | A1 | 3/2005 | Nightingale et al. |
| 2005/0165462 | A1 | 7/2005 | Bays et al. |
| 2005/0269582 | A1 | 12/2005 | Mueller et al. |
| 2005/0286955 | A1 | 12/2005 | Weeks et al. |
| 2006/0002131 | A1 | 1/2006 | Schultz et al. |
| 2006/0022211 | A1 | 2/2006 | Yatsuda et al. |
| 2006/0227570 | A1 | 10/2006 | Rutherford et al. |
| 2007/0001182 | A1 | 1/2007 | Schardt et al. |
| 2007/0051966 | A1 | 3/2007 | Higashi et al. |
| 2007/0297190 | A1 | 12/2007 | Ng |
| 2008/0079910 | A1 | 4/2008 | Rutherford et al. |
| 2008/0165523 | A1 * | 7/2008 | Schmidt ............. C09K 11/0883 |
| | | | 362/84 |

FOREIGN PATENT DOCUMENTS

| | | |
|---|---|---|
| JP | 2004146835 A | 5/2004 |
| JP | 2005205195 A | 8/2005 |
| JP | 2006049410 A | 2/2006 |
| JP | 2008504196 A | 2/2008 |
| WO | 2006011571 A1 | 2/2006 |
| WO | 2006054203 A1 | 5/2006 |
| WO | 2006104907 A1 | 10/2006 |

* cited by examiner

METHOD OF ILLUMINATION HAVING LIGHT EMITTING DEVICE WITH CERAMIC CONVERSION MATERIAL

This application claims the benefit or priority of and describes relationships between the following applications: wherein this application is a divisional of U.S. patent application Ser. No. 12/298,047, filed Oct. 22, 2008, which is the National Stage of International Application No. PCT/IB2007/051352, filed Apr. 16, 2007, which claims the priority of foreign application EP06113294.0 filed Apr. 26, 2006, all of which are incorporated herein in whole by reference.

This invention relates to the field of light delivery devices, especially light delivery devices which are used for medical purposes, such as endoscopy.

In endoscopy devices, light is delivered to a body lumen or body cavity, e.g. for diagnostic purposes as well as photodynamic therapy of atherosclerosis, malignant or benign tumor tissue, cancerous cells and other medical treatments. Devices of the prior art are disclosed in e.g. the US 2005/0165462, which is incorporated herein by reference.

Especially in endoscopy devices, which are used for diagnosis, a light source with a high flux density is used, such as Xenon lamps and halogen lamps. However, in prior art applications there is no possibility to change the color temperature of the light without deterioration of the light flux and/or light density. The term 'color temperature' is used in lieu of the definition of the correlated color temperature of a light source.

For example in halogen lamps it is possible to decrease the color temperature (increase the red emission relative to green and blue) by simply diminishing the light flux, but a shift towards the red while maintaining the light flux is impossible.

Such a change in color temperature on the other hand would allow a further facilitation of the diagnosis since it is known that e.g. by changing the color temperature the different tissues inside a patient's body, which is subjected to the endoscopy, appear differently on the picture made by the endoscopy camera. Therefore, it would be possible to improve the diagnosis by simply changing the color temperature and/or the spectral composition of the illumination.

It is therefore an object of the present invention to provide a light delivery device, especially a light delivery device for medical purposes, which allows a change in color temperature while essentially maintaining or even improving the light flux and/or light density.

This object is achieved by a light-emitting device having the features of Claim 1. Accordingly, a light delivery device, especially for medical lighting purposes, is provided comprising at least one light emitting device comprising at least one first LED which emits light in the wavelength range of ≥220 nm to ≤550 nm and at least one conversion element placed towards the at least one first LED, which converts at least partly the light from the at least one first LED to light in the wavelength range of ≥300 nm to ≤1000 nm, where the at least one conversion element comprises a ceramic conversion material.

By doing so, it is possible to realize a light delivery device which for most applications in the present invention has one or more of the following advantages:

Due to the ceramic conversion material, a high light flux density can be achieved, allowing the use of the light delivery device in a broad variety of applications, especially for endoscopical devices Due to the ceramic conversion material it is possible to change the color temperature of the light delivery device especially towards the "red" without a deterioration in light flux.

Due to the ceramic conversion material it is possible to increase the light flux without changing the geometrical properties of light generation and emission, maintaining the efficiency of any light collection optics.

According to the invention, the light-emitting device comprises at least one first LED which emits light in the wavelength range of ≥220 nm and ≤1000 nm. LEDs with an emittance in this wavelength range have proven themselves in practice.

Preferably, those LEDs consist of a AlInGaN electroluminescent device with a phosphor conversion element attached, absorbing at least partially LED emitted light and reemit that light at a wavelength larger than the LED emission wavelength.

According to a preferred embodiment of the present invention, the light emitting device comprises at least one first LED which emits light in the wavelength range of ≥250 nm and ≤800 nm, more preferably ≥300 nm and ≤780 nm.

The term "ceramic material" in the sense of the present invention means especially a crystalline or polycrystalline compact material or composite material with a controlled amount of pores or which is porefree.

The term "polycrystalline material" in the sense of the present invention means especially a material with a volume density larger than 90 percent of the main constituent, consisting of more than 80 percent of single crystal domains, with each domain being larger than 0.5 μm in diameter and having different crystallographic orientations. The single crystal domains may be connected by amorphous or glassy material or by additional crystalline constituents.

According to a preferred embodiment of the present invention, the at least one conversion element has a refractive index n of ≥1.5 and ≤3 and the ratio A:E is ≥2:1 and ≤50000:1, where A and E are defined as follows:

the at least one conversion element comprises at least one entrance surface where light emitted by the at least one LED can enter the conversion element, and at least one exit surface, where light can exit the at least one conversion element, each of the at least one entrance surfaces having an entrance surface area, the entrance surface area(s) being numbered $A_1 \ldots A_n$ and each of the at least one exit surfaces having an exit surface area, the exit surface area(s) being numbered $E_1 \ldots E_n$ and the sum of each of the at least one entrance surface areas A being $A=A_1+A_2 \ldots +A_n$ and the sum of each of the at least one exit surface areas E being $E=E_1+E_2 \ldots +E_n$ By doing so, it is possible for most applications within the present invention to realize a lamp combining a high light flux with a greatly increased luminance compared to the LED.

According to a preferred embodiment of the invention, the light emitting device comprises at least one conversion element which comprises at least one entrance surface A where light emitted by the at least one LED can enter the conversion element. After absorption, light reemitted by the conversion element can leave through the entrance surface only with the fraction emitted within the escape cone of the material. The main fraction of the emitted light will be trapped within the conversion element and guided to an exit surface by total internal reflection.

In order to enhance this process, this at least one entrance surface has according to a preferred embodiment of the present invention a roughness Ra of ≥1 nm and ≤500 nm, preferably ≥10 nm and ≤100 nm and more preferably ≥20 nm and ≤40 nm. By this effect it is possible indeed to concentrate light at the exit surface E of the light conversion element.

According to a preferred embodiment of the present invention, the LEDs are in direct contact with the conversion elements but each have a lower refractive index than the conversion elements.

However, according to another preferred embodiment of the present invention, the LEDs and the conversion elements are placed at a distance from each other. In this case, preferably, the distance between the conversion elements and the LEDs is ≥1 µm and ≤100 mm, preferably ≥100 µm and ≤10 mm and more preferably ≥1 mm and ≤5 mm.

Besides the optical function of the separation of the LEDs and the conversion layer it is also advantageous and, insofar a further preferred embodiment of the present invention is concerned, to have a thermal decoupling of the conversion layer and the LEDs. In most applications, the efficiency of the conversion process decreases significantly for temperatures well above 100° C. In another preferred embodiment of this invention special cooling means are applied to the light-emitting device to dissipate heat generated within the conversion layer and the LED(s) to a heat sink outside the device, the LED(s) and the conversion element(s) being placed at a distance from each other preferably as described above. This cooling can be realized by forced air blowing and/or by liquid cooling, pumping a liquid around the conversion layer. In this preferred embodiment of the present invention the cooling means is therefore a liquid, preferably selected from a group comprising Water-, Oils, Propylene-, Ethylene-, Glycol based systems and mixtures thereof. In the latter case the refractive index of the liquid should be as low as possible to prevent light extraction of emitted light through the surface A of the conversion layer. The difference of the refractive index of the conversion layer $n_c$ and the liquid $n_l$ should be $0.1 \leq n_c - n_l \leq 3$, preferably $0.3 \leq n_c - n_l \leq 2.5$ and more preferably $0.5 \leq n_c - n_l \leq 2$.

According to the invention, the light that enters the conversion element is at least partly converted to light in the wavelength range of ≥300 nm and ≤1000 nm. By doing so, the light emitting device will emit light in a wavelength range, which is suitable for a broad variety of applications. According to a preferred embodiment of the present invention, the light that enters the conversion element is at least partly converted to light in the wavelength range of ≥350 nm and ≤880 nm, more preferably ≥380 nm and ≤780 nm.

According to a preferred embodiment of the invention, the conversion element comprises at least one exit surface, where light can exit the conversion element. In order to enhance this, according to a preferred embodiment of the present invention, the at least one exit surface is equipped with a refractive and/or diffractive structure or surface. This includes that the at least one exit surface is equipped with a scattering structure, a pyramid-like structure, a micro lens structure or a compound parabolic concentrator (CPC). The exit surface may contain one or a plurality of the indicated structures. The geometry of the exit structure can also be used to direct the emitted light from the exit surface to meet any requirement of an application.

According to a preferred embodiment of the invention, the at least one exit surface is optically directly coupled to a light guiding structure, by coupling the light conversion element to a light guide with a medium having an refractive index $n_c$ close to the refractive index of either the conversion element $n_{conv}$ or the light guide $n_g$. The minimum of the difference of $(abs(n_c - n_{conv})$ and $abs(n_c - n_g)$ is preferably <0.3, more preferably <0.1 and most preferably <0.01.

According to a preferred embodiment of the invention, each of the at least one entrance surfaces has an entrance surface area, the entrance surface areas being numbered $A_1 \ldots A_n$ and each of the at least one exit surfaces has an exit surface area, the exit surface areas being numbered $E_1 \ldots E_n$ and the sum of each of the at least one entrance surface areas $A_n$ is $A = A_1 + A_2 \ldots + A_n$ and the sum of each of the at least one exit surface areas $E_n$ is $E = E_1 + E_2 \ldots + E_n$ and the ratio A:E, A and E being as defined above, is ≥2:1 and ≤50000:1.

By doing so, the light flux of the LED can be set within the preferred and desired range. According to a preferred embodiment of the present invention, the ratio A:E, A and E being as defined above, is ≥5:1 and ≤5000:1, more preferably ≥10:1 and ≤3000:1 yet more preferably ≥20:1 and ≤1000:1, and most preferably ≥50:1 and ≤500:1.

According to a preferred embodiment of the invention, the at least one conversion element has an refractive index n of ≥1.5 and ≤3. By doing so, it can be easily achieved that the efficiency of the LED is within a desired range. Especially, by setting the refractive index as described, the light that enters the conversion element as described will undergo total reflection at the sides/surfaces of the conversion element, which are no exit surfaces. The fraction of the light from the LEDs which is emitted through the exit surface (possibly after conversion) of the conversion element compared to the total emitted light can be as high as $$1 - \frac{1}{2n^2},$$

with n being the refractive index of the conversion element. This results in a very highly efficient light-emitting device. Preferably the at least one conversion element has a refractive index n of ≥1.5 and ≤2.8, more preferably ≥1.7 and ≤2.6

According to a preferred embodiment of the present invention, the transmittance for emitted light of the conversion element is ≥8 and ≤1. This greatly enhances the efficiency of the light-emitting device. Preferably, the transmittance of the conversion element is ≥9 and ≤1, more preferably ≥0.95 and ≤1.

According to a preferred embodiment of the present invention, the relation of the quantum efficiency at a temperature T compared to the quantum efficiency at 20° C. (thermal quenching) of the conversion element is ≥70% and ≤100% at 100° C., preferably ≥80% and ≤100% at 100° C. and most preferably ≥90% and ≤100% at 100° C.

According to a preferred embodiment of the present invention, the temperature at which the quantum efficiency of the conversion layer is reduced to 50% compared to the quantum efficiency at room temperature, (=$TQ_{50\%}$-value), is ≥120° C. and ≤300° C., preferably 150° C.≤$TQ_{50\%}$≤350° C. and more preferably 180° C.≤$TQ_{50\%}$≤400° C.

According to a preferred embodiment of the present invention, the light delivery device comprises at least one further auxiliary LED which emits in the wavelength of ≥220 nm to ≤600 nm.

By doing so, it is possible in most applications within the present invention to very easily shift the color temperature of the light provided by the light delivery device without lowering the original light flux.

According to a preferred embodiment of the present invention, the auxiliary LEDs have (combined) a power of 2% to 100% of the first LED. In case that more than one first LED is present, it is preferred that the auxiliary LEDs have (combined) a power of ≥10% to ≤1000% of the combined first LEDs.

According to a preferred embodiment of the present invention, the auxiliary LEDs are mounted either individually or in a die package on a single supporting plate serving as a heat conductor and providing the electrical contacts for operation. The one or more supporting plates may also contain active electronic elements for LED protection, operation and control. In addition, according to a preferred embodiment of the present invention the auxiliary LEDs on a supporting plate are covered with optical structures to optimise the light output of the auxiliary LEDs.

In a further preferred embodiment of the present invention, the auxiliary LEDs are mounted on a supporting plate with a packing density of ≥0.05 and ≤0.5, preferably ≥0.1 and ≤0.3. The packing density is the ratio of the sum of the LED die surface areas divided by the surface area of the supporting plate. By doing so, it is possible to realize a light emitting device with particularly high lumen flux and superior luminance at a high power efficiency, which is achieved by effective cooling of the auxiliary LEDs, keeping the junction temperature below the specified values of the auxiliary LEDs.

According to a preferred embodiment of the present invention, the light from the at least one first LED is sent to the at least one conversion element in a preferred first light propagation direction and the light sent from the auxiliary LEDs towards the at least one conversion element has an angle towards the preferred first light direction of ≥65° and ≤115°, preferably ≥75° and ≤105° and most preferably 85° and 95°.

In such an arrangement it is possible in most applications within the present invention to ensure that the light that is emitted by the auxiliary LEDs is only or essentially used for conversion inside the conversion element, thereby allowing to "add" light of a certain wavelength.

According to a preferred embodiment of the present invention, the auxiliary LEDs are placed inside a support tube.

Preferably the part of the support tube, where no auxiliary LEDs are placed, is preferably covered with a highly reflective coating, preferably a mirror or a dielectric coating or a mixture thereof. By doing so, the efficiency of the conversion element(s) and the light emitting device can be enhanced further. The mirror is preferably applied by sputtering or evaporation in vacuum directly on the at least one further surface which is neither an exit nor an entrance surface. The mirror material is preferably selected from a group comprising silver, aluminum and/or mixtures thereof. The thickness of the mirror is preferably ≥50 nm and ≤1000 nm.

In such an arrangement it is possible in most applications within the present invention to ensure that the light that is emitted by the auxiliary LEDs is only or essentially used for conversion inside the conversion element, thereby allowing to "add" light of a certain wavelength and lowering the power requirements of the LEDs.

According to a preferred embodiment of the invention, the glass phase ratio of the ceramic conversion material is ≥2% to ≤5%, according to an embodiment of the present invention, ≥3% to ≤4%. It has been shown in practice that materials with such a glass phase ratio show the improved characteristics, which are advantageous and desired for the present invention.

The term "glass phase" in the sense of the present invention means especially non-crystalline grain boundary phases, which may be detected by scanning electron microscopy or transmission electron microscopy.

According to a preferred embodiment of the present invention, the surface roughness RMS (disruption of the planarity of a surface; measured as the geometric mean of the difference between highest and deepest surface features) of the surface(s) of the ceramic conversion material and/or the conversion element(s) is ≥0.001 µm and ≤100 µm. According to one embodiment of the present invention, the surface roughness of the surface(s) of the ceramic conversion material and/or the conversion element(s) is ≥0.01 µm and ≤10 µm, according to another embodiment of the present invention ≥0.1 µm and ≤5 µm, according to yet another embodiment of the present invention ≥0.15 µm and ≤3 µm, and according to still another embodiment of the present invention ≥0.2 µm and ≤2 µm.

According to a preferred embodiment of the present invention, the specific surface area of the ceramic conversion material and/or the conversion element(s) is ≥$10^{-7}$ m$^2$/g and ≤1 m$^2$/g.

According to a preferred embodiment of the present invention, the ceramic conversion material is essentially made of material selected from the group of $(M^I_{1-x-y}M^{II}_xM^{III}_y)_3(M^{IV}_{1-z}M^V_z)_5O_{12}$—where $M^I$ is selected from the group comprising Y, Lu or mixtures thereof, $M^{II}$ is selected from the group comprising Gd, La, Yb or mixtures thereof, $M^{III}$ is selected from the group comprising Tb, Pr, Ce, Er, Nd, Eu or mixtures thereof, $M^{IV}$ is Al, $M^V$ is selected from the group comprising Ga, Sc or mixtures thereof, and 0≤x≤1, 0≤y≤0.1, 0≤z≤1, $(M^I_{1-x-y}M^{II}_xM^{III}_y)_2O_3$—where $M^I$ is selected from the group comprising Y, Lu or mixtures thereof, $M^{II}$ is selected from the group comprising Gd, La, Yb or mixtures thereof, $M^{III}$ is selected from the group comprising Tb, Pr, Ce, Er, Nd, Eu, Bi, Sb or mixtures thereof, and 0≤x≤1, 0≤y≤0.1, $(M^I_{1-x-y}M^{II}_xM^{III}_y)S_{1-z}Se_z$—where $M^I$ is selected from the group comprising Ca, Sr, Mg, Ba or mixtures thereof, $M^{II}$ is selected from the group comprising Ce, Eu, Mn, Tb, Sm, Pr, Sb, Sn or mixtures thereof, $M^{III}$ is selected from the group comprising K, Na, Li, Rb, Zn or mixtures thereof, and 0≤x≤0.01, 0≤y≤0.05, 0≤z≤1, $(M^I_{1-x-y}M^{II}_xM^{III}_y)O$—where $M^I$ is selected from the group comprising Ca, Sr, Mg, Ba or mixtures thereof, $M^{II}$ is selected from the group comprising Ce, Eu, Mn, Tb, Sm, Pr or mixtures thereof, $M^{III}$ is selected from the group comprising K, Na, Li, Rb, Zn or mixtures thereof, and 0≤x≤0.1, 0≤y≤0.1, $(M^I_{2-x}M^{II}_xM^{III}_2)O_7$—where $M^I$ is selected from the group comprising La, Y, Gd, Lu, Ba, Sr or mixtures thereof, $M^{II}$ is selected from the group comprising Eu, Tb, Pr, Ce, Nd, Sm, Tm or mixtures thereof, $M^{III}$ is selected from the group comprising Hf, Zr, Ti, Ta, Nb or mixtures thereof, and 0≤x≤1, $(M^I_{1-x}M^{II}_xM^{III}_{1-y}M^{IV}_y)O_3$—where $M^I$ is selected from the group comprising Ba, Sr, Ca, La, Y, Gd, Lu or mixtures thereof, $M^{II}$ is selected from the group comprising Eu, Tb, Pr, Ce, Nd, Sm, Tm or mixtures thereof, $M^{III}$ is selected from the group comprising Hf, Zr, Ti, Ta, Nb or mixtures thereof, and $M^{IV}$ is selected from the group comprising Al, Ga, Sc, Si or mixtures thereof, and 0≤x≤0.1, 0≤y≤0.1.

According to a preferred embodiment of the present invention, the conversion element comprises at least one further surface which is neither an exit nor an entrance surface and where at least one, preferably all of said further surface(s) are covered with a reflective coating, preferably a mirror or a dielectric coating or a mixture thereof. By doing so, the efficiency of the conversion element(s) and the light emitting device can be enhanced further. The mirror is preferably applied by sputtering or evaporation in vacuum directly on the at least one further surface, which is neither an exit nor an entrance surface. The mirror material is preferably selected from a group comprising silver, aluminum and/or mixtures thereof. The thickness of the mirror is preferably ≥50 nm and ≤1000 nm A light emitting device according to the present invention may be of use in a wide variety of systems and/or applications, amongst them one or more of the following:
  medical lighting application systems,
  endoscopes
  devices for photodynamic therapy The aforementioned components, as well as the claimed components and the components to be used in accordance with the invention in the described embodiments, are not subject to any special exceptions with respect to their size, shape, material selection and technical concept such that the selection criteria known in the pertinent field can be applied without limitations.

Additional details, features, characteristics and advantages of the object of the invention are disclosed in the subclaims, figures, examples and the following description of the respective figures and examples—which in an exemplary fashion—show several preferred embodiments and examples of a light delivery device according to the invention, wherein:

Figure 1:
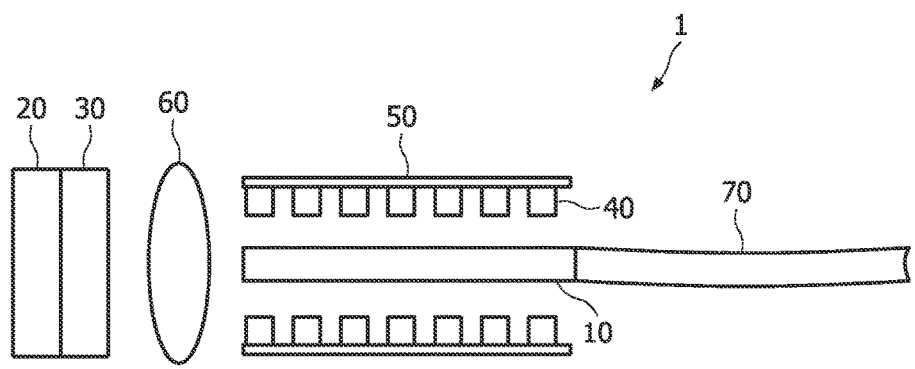
FIG. 1 shows a very schematic cross-sectional partial view of a light delivery device according to a first embodiment of the present invention.

FIG. 1 shows a very schematic cross-sectional partial view of a light delivery device 1 according to a first embodiment of the present invention. The light delivery device 1 comprises a first LED 20, a first converter substance 30, which projects light towards the conversion element 10 through a collector lens 60. From the conversion element 10, the light is then partially converted and projected towards the optical fibre 70. The optical fibre then may e.g. lead the light towards the tip of an endoscopy device (not shown in the Fig.).

In order to shift the color temperature of the LED, several auxiliary LEDs 40 are provided on a support tube 50; this part of the embodiment will be described in more detail in FIG. 3, which is an enlarged partial view of this part of the light delivery device.

As can be best seen from FIG. 1, the angle between the preferred light direction from the first LED (which in this embodiment is essentially horizontal) and the light sent out from the auxiliary LEDs (which in this embodiment is essentially vertical) is approximately 90°.

Figure 2:
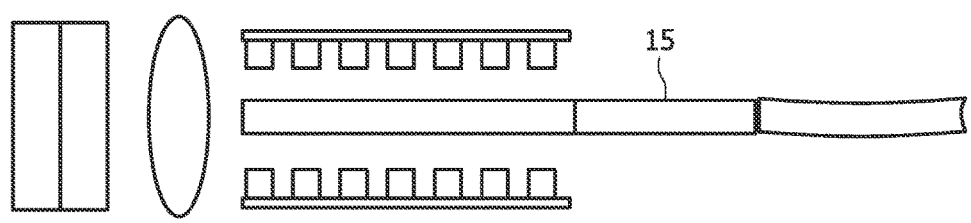
FIG. 2 shows a very schematic cross-sectional partial view of a light delivery device according to a first embodiment of the present invention.

FIG. 2 shows a very schematic cross-sectional partial view of a light delivery device according to a first embodiment of the present invention. This second embodiment is identical with that of FIG. 1 except that a second conversion element 15 is present.

Figure 3:
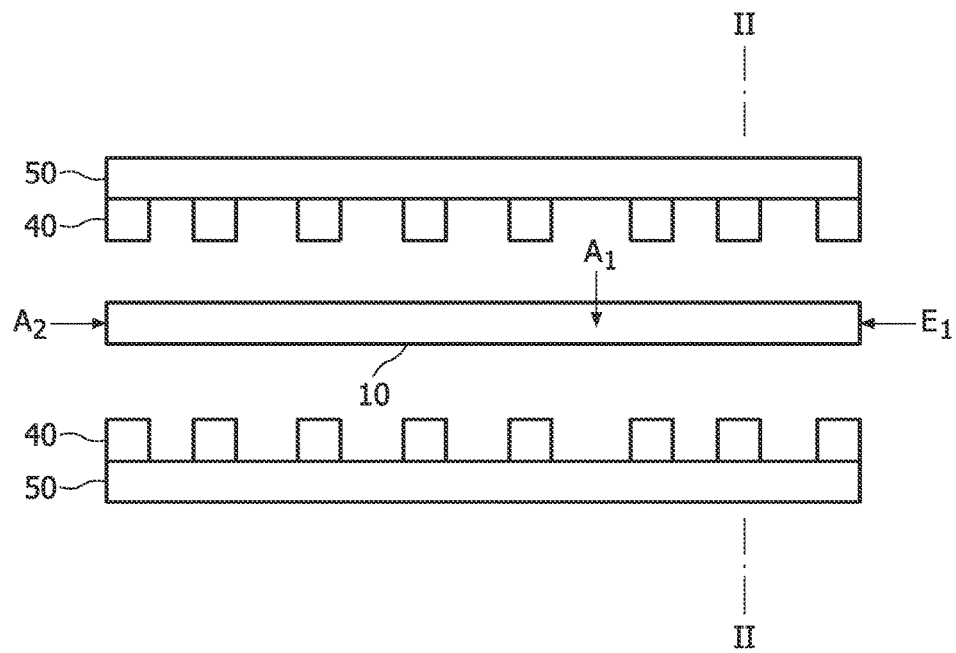
FIG. 3 shows a schematic cross-sectional partial view of the embodiment of FIG. 1 along line IV-IV in FIG. 4
Figure 4:
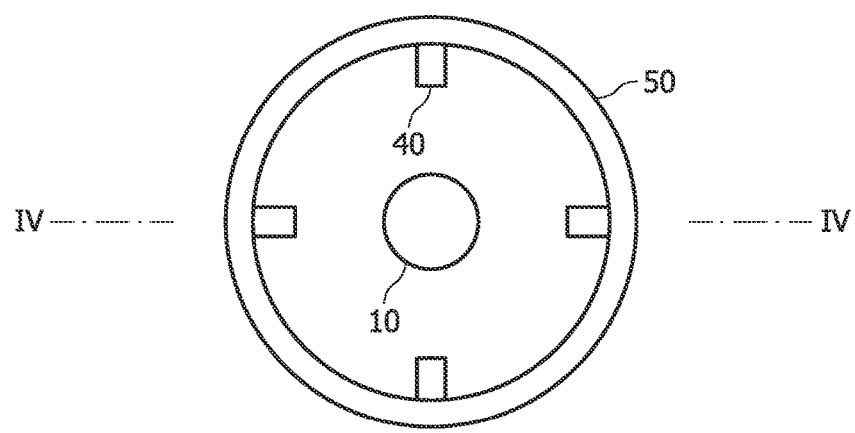
FIG. 4 shows a cross-sectional view of the conversion element of the light delivery device of FIGS. 1 and 3 along line II-II in FIG. 3

FIG. 3 shows a schematic cross-sectional partial view the embodiment of FIG. 1 along line IV-IV in FIG. 4.

FIG. 4 shows a cross-sectional view of the conversion element of the light delivery device of FIGS. 1 and 3 along line II-II in FIG. 3.

As can be seen from FIGS. 3 and 4, the conversion element 10 is somewhat cylindrical in shape and preferably matches the optical fibre 70. It is circumferentially surrounded by the support tube 50, which holds several sets of auxiliary LEDs 40. In this embodiment, four rows of auxiliary LEDs were used; however, it goes without saying that more (or less) auxiliary LEDs may be used, depending on the actual application. The inside surface of the support tube where no LEDs are located, is covered with a mirror.

Preferably, the auxiliary LEDs are arranged closely in groups, e.g. rows, leaving large contiguous areas of the supporting tube coated with a highly reflective coating. By doing so, the total amount of LED light absorbed by the conversion element is maximized.

The conversion element 10 has two entrance surfaces $A_1$, $A_2$ ($A_2$ being the "side" of the cylinder that projects towards the LED 20), resulting in an A being $A_1+A_2$. Since there is only one exit surface with an exit surface area $E_1$, the numeral E, being the sum of each of the at least one exit surface areas would simply be $E=E_1$. The ratio of A:E is set to be 10:1 and 10000:1; in this example A:E would be approximately 400:1. However, it should be noted, that the embodiment in FIGS. 3 and 4 is highly schematic and the ratio may be different for other applications.

Figure 5:
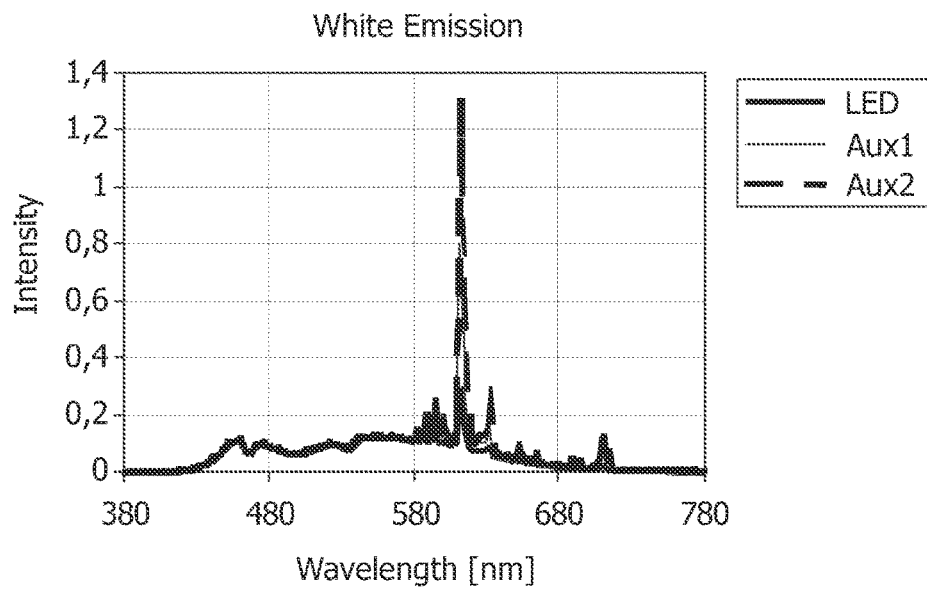
FIG. 5 shows a graph showing three emission spectra of a light delivery device according to a first example of the invention.
Figure 6:
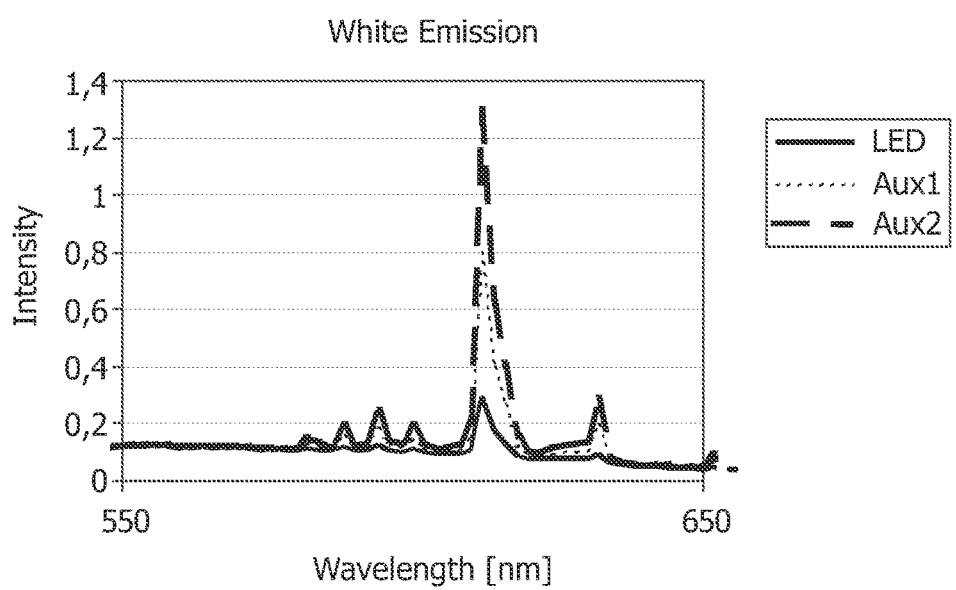
FIG. 6 shows an enlarged section of the graph of FIG. 5.
Figure 7:
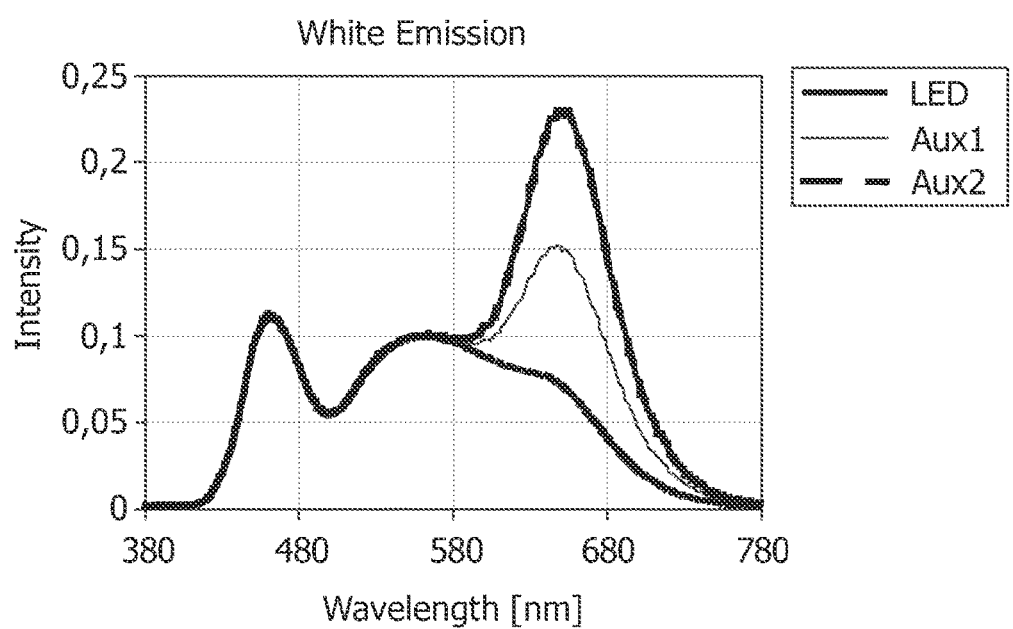
FIG. 7 shows a graph showing three emission spectra of a light delivery device according to a second example.

The lighting device according to the invention is—in a merely exemplarily fashion—furthermore illustrated by the following examples together with the FIGS. 5 to 7:

FIG. 5 shows a graph showing three emission spectra of a light delivery device according to a first example of the invention, FIG. 6 shows a enlarged section of the graph of FIG. 5.

EXAMPLE I

In Example I, a light delivery device with the setting of FIG. 1 was used. The first LED (reference no. 20 in FIG. 1) was a InGaN LED with a peak emission at 462 nm, the first converter substance (reference no. 30 in FIG. 1) was a YAG:Ce ceramic material with the composition $Y_{(3-x-y)}Gd_xAl_5O_{12}:Ce_y$ with x=0.3 and y=0.06.

The conversion element (reference no. 10 in FIG. 1) was $Y_2O_3$:Eu with a 7% Europium doping and a density of 5.029 g/cm³.

The light delivery device furthermore comprises two sets of auxiliary LEDs (reference no. 40 in FIG. 1), which are also InGaN LEDs. Each set of LEDs has a power of 100% of the first LED and a peak emission at 465 nm.

FIGS. 5 and 6 show the spectra of the light delivery device with the first LED only ("LED"), with one set of auxiliary LEDs switched on ("Aux1") and with both sets of auxiliary LEDs switched on ("Aux2").

The data of FIGS. 5 and 6 are listed in Table I

TABLE I

|     | LED      | Aux1     | Aux2     |
| --- | -------- | -------- | -------- |
| 380 | 0.00188  | 0.00238  | 0.00288  |
| 382 | 0.001739 | 0.002239 | 0.002739 |
| 384 | 0.000654 | 0.001154 | 0.001654 |
| 386 | 0.000711 | 0.001211 | 0.001711 |
| 388 | 0.001233 | 0.001733 | 0.002233 |
| 390 | 0.00117  | 0.00167  | 0.00217  |
| 392 | 0.000811 | 0.001311 | 0.001811 |
| 394 | 0.000946 | 0.001446 | 0.001946 |
| 396 | 0.000838 | 0.001338 | 0.001838 |
| 398 | 0.000623 | 0.001123 | 0.001623 |
| 400 | 0.001035 | 0.001535 | 0.002035 |
| 402 | 0.001292 | 0.001792 | 0.002292 |
| 404 | 0.00122  | 0.00172  | 0.00222  |
| 406 | 0.001175 | 0.001675 | 0.002175 |
| 408 | 0.001278 | 0.001778 | 0.002278 |
| 410 | 0.001367 | 0.001867 | 0.002367 |
| 412 | 0.00144  | 0.00194  | 0.00244  |
| 414 | 0.001532 | 0.002032 | 0.002532 |
| 416 | 0.001929 | 0.002429 | 0.002929 |
| 418 | 0.002528 | 0.003028 | 0.003528 |
| 420 | 0.003352 | 0.003852 | 0.004352 |
| 422 | 0.004891 | 0.005391 | 0.005891 |
| 424 | 0.006672 | 0.007172 | 0.007672 |
| 426 | 0.008475 | 0.008975 | 0.009475 |
| 428 | 0.011025 | 0.011525 | 0.012025 |
| 430 | 0.014129 | 0.014629 | 0.015129 |
| 432 | 0.01841  | 0.01891  | 0.01941  |
| 434 | 0.023055 | 0.023555 | 0.024055 |
| 436 | 0.027142 | 0.027642 | 0.028142 |
| 438 | 0.032944 | 0.033444 | 0.033944 |
| 440 | 0.040675 | 0.041175 | 0.041675 |
| 442 | 0.047448 | 0.047948 | 0.048448 |
| 444 | 0.057997 | 0.058497 | 0.058997 |
| 446 | 0.06568  | 0.06618  | 0.06668  |
| 448 | 0.076898 | 0.077398 | 0.077898 |
| 450 | 0.088318 | 0.088818 | 0.089318 |
| 452 | 0.097781 | 0.098281 | 0.098781 |
| 454 | 0.103529 | 0.104029 | 0.104529 |
| 456 | 0.107177 | 0.107677 | 0.108177 |
| 458 | 0.109494 | 0.109994 | 0.110494 |
| 460 | 0.110901 | 0.111401 | 0.111901 |
| 462 | 0.093512 | 0.094012 | 0.094512 |
| 464 | 0.078426 | 0.078926 | 0.079426 |
| 466 | 0.065164 | 0.066119 | 0.067074 |
| 468 | 0.068973 | 0.070108 | 0.071243 |
| 470 | 0.08761  | 0.08811  | 0.08861  |
| 472 | 0.096669 | 0.097169 | 0.097669 |
| 474 | 0.100671 | 0.101351 | 0.102031 |
| 476 | 0.098311 | 0.098811 | 0.099311 |
| 478 | 0.093635 | 0.094135 | 0.094635 |
| 480 | 0.088668 | 0.089168 | 0.089668 |
| 482 | 0.085616 | 0.086116 | 0.086616 |
| 484 | 0.083357 | 0.083857 | 0.084357 |
| 486 | 0.079624 | 0.080124 | 0.080624 |
| 488 | 0.073583 | 0.074083 | 0.074583 |
| 490 | 0.070694 | 0.071414 | 0.072134 |
| 492 | 0.068335 | 0.068835 | 0.069335 |
| 494 | 0.064839 | 0.065339 | 0.065839 |
| 496 | 0.063057 | 0.063557 | 0.064057 |
| 498 | 0.062375 | 0.062875 | 0.063375 |
| 500 | 0.062363 | 0.062993 | 0.063623 |
| 502 | 0.062725 | 0.06337  | 0.064015 |
| 504 | 0.063773 | 0.064273 | 0.064773 |
| 506 | 0.068184 | 0.070894 | 0.073604 |
| 508 | 0.072833 | 0.078278 | 0.083723 |
| 510 | 0.076638 | 0.079698 | 0.082758 |
| 512 | 0.080117 | 0.080647 | 0.081177 |
| 514 | 0.084271 | 0.085041 | 0.085811 |
| 516 | 0.088583 | 0.089083 | 0.089583 |
| 518 | 0.092116 | 0.092726 | 0.093336 |
| 520 | 0.096028 | 0.096528 | 0.097028 |
| 522 | 0.098354 | 0.098854 | 0.099354 |
| 524 | 0.095827 | 0.096327 | 0.096827 |
| 526 | 0.094712 | 0.095212 | 0.095712 |
| 528 | 0.093644 | 0.094144 | 0.094644 |

TABLE I-continued

|     | LED      | Aux1     | Aux2       |
| --- | -------- | -------- | ---------- |
| 530 | 0.086809 | 0.087309 | 0.087809   |
| 532 | 0.079557 | 0.080057 | 0.080557   |
| 534 | 0.078023 | 0.083963 | 0.089903   |
| 536 | 0.081832 | 0.083412 | 0.084992   |
| 538 | 0.096771 | 0.099706 | 0.102641   |
| 540 | 0.107926 | 0.110741 | 0.113556   |
| 542 | 0.116971 | 0.117571 | 0.118171   |
| 544 | 0.121157 | 0.121782 | 0.122407   |
| 546 | 0.122688 | 0.123223 | 0.123758   |
| 548 | 0.122018 | 0.122573 | 0.123128   |
| 550 | 0.121649 | 0.122704 | 0.123759   |
| 552 | 0.121918 | 0.124548 | 0.127178   |
| 554 | 0.122846 | 0.125451 | 0.128056   |
| 556 | 0.123639 | 0.125474 | 0.127309   |
| 558 | 0.123114 | 0.123614 | 0.124114   |
| 560 | 0.122137 | 0.122637 | 0.123137   |
| 562 | 0.121608 | 0.122568 | 0.123528   |
| 564 | 0.120783 | 0.122688 | 0.124593   |
| 566 | 0.119735 | 0.12131  | 0.122885   |
| 568 | 0.118723 | 0.120298 | 0.121873   |
| 570 | 0.118546 | 0.120606 | 0.122666   |
| 572 | 0.116935 | 0.11762  | 0.118305   |
| 574 | 0.115054 | 0.115614 | 0.116174   |
| 576 | 0.113432 | 0.114262 | 0.115092   |
| 578 | 0.109946 | 0.111191 | 0.112436   |
| 580 | 0.107852 | 0.110017 | 0.112182   |
| 582 | 0.113155 | 0.13106  | 0.148965   |
| 584 | 0.110682 | 0.124317 | 0.137952   |
| 586 | 0.10715  | 0.11296  | 0.11877    |
| 588 | 0.120096 | 0.159521 | 0.198946   |
| 590 | 0.107076 | 0.118441 | 0.129806   |
| 592 | 0.106777 | 0.118612 | 0.130447   |
| 594 | 0.126511 | 0.186606 | 0.246701   |
| 596 | 0.106581 | 0.124741 | 0.142901   |
| 598 | 0.103291 | 0.118781 | 0.134271   |
| 600 | 0.112167 | 0.152797 | 0.193427   |
| 602 | 0.100955 | 0.120695 | 0.140435   |
| 604 | 0.094712 | 0.104957 | 0.115202   |
| 606 | 0.094031 | 0.107736 | 0.121441   |
| 608 | 0.094532 | 0.114652 | 0.134772   |
| 610 | 0.105648 | 0.156603 | 0.207558   |
| 612 | 0.299    | 0.799    | 1.299      |
| 614 | 0.175572 | 0.397937 | 0.60.620302 |
| 616 | 0.134533 | 0.268638 | 0.402743   |
| 618 | 0.088959 | 0.124684 | 0.160409   |
| 620 | 0.077779 | 0.093569 | 0.109359   |
| 622 | 0.074426 | 0.088086 | 0.101746   |
| 624 | 0.075279 | 0.096684 | 0.118089   |
| 626 | 0.074294 | 0.099299 | 0.124304   |
| 628 | 0.073762 | 0.103197 | 0.132632   |
| 630 | 0.073588 | 0.107703 | 0.141818   |
| 632 | 0.098097 | 0.193427 | 0.288757   |
| 634 | 0.060529 | 0.075204 | 0.089879   |
| 636 | 0.055331 | 0.062916 | 0.070501   |
| 638 | 0.052421 | 0.058256 | 0.064091   |
| 640 | 0.049973 | 0.054533 | 0.059093   |
| 642 | 0.047951 | 0.052381 | 0.056811   |
| 644 | 0.045942 | 0.050327 | 0.054712   |
| 646 | 0.044127 | 0.048317 | 0.052507   |
| 648 | 0.042124 | 0.045564 | 0.049004   |
| 650 | 0.040988 | 0.045618 | 0.050248   |
| 652 | 0.048088 | 0.072903 | 0.097718   |
| 654 | 0.039911 | 0.050101 | 0.060291   |
| 656 | 0.03537  | 0.038875 | 0.04238    |
| 658 | 0.034343 | 0.039013 | 0.043683   |
| 660 | 0.031902 | 0.034377 | 0.036852   |
| 662 | 0.031165 | 0.035045 | 0.038925   |
| 664 | 0.034241 | 0.048226 | 0.062211   |
| 666 | 0.02811  | 0.030955 | 0.0338     |
| 668 | 0.0265   | 0.0287   | 0.0309    |
| 670 | 0.025269 | 0.027384 | 0.029499   |
| 672 | 0.023972 | 0.026072 | 0.028172   |
| 674 | 0.02249  | 0.02391  | 0.02533   |
| 676 | 0.0213   | 0.022575 | 0.02385   |
| 678 | 0.020134 | 0.021254 | 0.022374   |
| 680 | 0.019324 | 0.020729 | 0.022134   |
| 682 | 0.01838  | 0.019505 | 0.02063    |
| 684 | 0.017914 | 0.019504 | 0.021094   |

TABLE I-continued

| | LED | Aux1 | Aux2 |
|---|---|---|---|
| 686 | 0.017255 | 0.01919 | 0.021125 |
| 688 | 0.021362 | 0.034522 | 0.047682 |
| 690 | 0.017832 | 0.024502 | 0.031172 |
| 692 | 0.014795 | 0.01648 | 0.018165 |
| 694 | 0.017148 | 0.026443 | 0.035738 |
| 696 | 0.013255 | 0.015435 | 0.017615 |
| 698 | 0.0121 | 0.01304 | 0.01398 |
| 700 | 0.011542 | 0.012727 | 0.013912 |
| 702 | 0.011226 | 0.012981 | 0.014736 |
| 704 | 0.011728 | 0.015483 | 0.019238 |
| 706 | 0.013805 | 0.023045 | 0.032285 |
| 708 | 0.026806 | 0.066926 | 0.107046 |
| 710 | 0.029198 | 0.076303 | 0.123408 |
| 712 | 0.013137 | 0.024182 | 0.035227 |
| 714 | 0.018797 | 0.043992 | 0.069187 |
| 716 | 0.008111 | 0.009701 | 0.011291 |
| 718 | 0.00744 | 0.008405 | 0.00937 |
| 720 | 0.006897 | 0.007732 | 0.008567 |
| 722 | 0.006787 | 0.007587 | 0.008387 |
| 724 | 0.006289 | 0.006994 | 0.007699 |
| 726 | 0.005959 | 0.006624 | 0.007289 |
| 728 | 0.005447 | 0.006077 | 0.006707 |
| 730 | 0.005466 | 0.006141 | 0.006816 |
| 732 | 0.005346 | 0.005961 | 0.006576 |
| 734 | 0.004935 | 0.005435 | 0.005935 |
| 736 | 0.004677 | 0.005177 | 0.005677 |
| 738 | 0.004646 | 0.005146 | 0.005646 |
| 740 | 0.004793 | 0.005293 | 0.005793 |
| 742 | 0.004545 | 0.0056 | 0.006655 |
| 744 | 0.004599 | 0.006199 | 0.007799 |
| 746 | 0.003901 | 0.004401 | 0.004901 |
| 748 | 0.003995 | 0.00496 | 0.005925 |
| 750 | 0.003715 | 0.004215 | 0.004715 |
| 752 | 0.003625 | 0.004125 | 0.004625 |
| 754 | 0.003318 | 0.003818 | 0.004318 |
| 756 | 0.003133 | 0.003633 | 0.004133 |
| 758 | 0.003193 | 0.003693 | 0.004193 |
| 760 | 0.00308 | 0.00358 | 0.00408 |
| 762 | 0.003095 | 0.003595 | 0.004095 |
| 764 | 0.002751 | 0.003251 | 0.003751 |
| 766 | 0.002666 | 0.003166 | 0.003666 |
| 768 | 0.002573 | 0.003073 | 0.003573 |
| 770 | 0.002335 | 0.002835 | 0.003335 |
| 772 | 0.002312 | 0.002812 | 0.003312 |
| 774 | 0.001938 | 0.002438 | 0.002938 |
| 776 | 0.001862 | 0.002362 | 0.002862 |
| 778 | 0.001972 | 0.002472 | 0.002972 |
| 780 | 0.001951 | 0.002451 | 0.002951 |

Further data of Example I are given in Table II:

TABLE II

| | LED | Aux1 | Aux2 |
|---|---|---|---|
| CCT [K] | 4491 | 3481 | 2865 |
| Ra | 80 | 88 | 85 |
| uv | 0.011 | 0.002 | 0.009 |
| x | 0.3662 | 0.4043 | 0.4331 |
| Y | 0.3923 | 0.3857 | 0.3807 |
| LE [lmW] | 343 | 334 | 327 |
| R1 | 77.7 | 94.2 | 97 |
| R2 | 89.4 | 99 | 92.1 |
| R3 | 95.6 | 93.9 | 87.6 |
| R4 | 72.6 | 88.4 | 94.7 |
| R5 | 76.1 | 92.1 | 97 |
| R6 | 85.8 | 93.2 | 80.9 |
| R7 | 83.6 | 82.1 | 76.2 |
| R8 | 57.2 | 61.9 | 56.5 |
| R9 | 14.9 | 9.9 | 7.2 |
| R10 | 73.8 | 96.1 | 88.9 |
| R11 | 68.6 | 88 | 96.7 |
| R12 | 57.3 | 79.8 | 76.2 |
| R13 | 80.6 | 96.9 | 94.7 |
| R14 | 97.4 | 98.8 | 96 |

It can be clearly seen that a shift of the color temperature over approx. 1600K is possible without any deterioration of the lighting properties, such as the color rendering index Ra of the light delivery device.

FIG. 7 shows a graph with three emission spectra of a light delivery device according to a second example of the invention.

EXAMPLE II

In Example II, a light delivery device with the setting of FIG. 1 was used. The first LED (reference no. 20 in FIG. 1) was an InGaN LED with a peak emission at 462 nm, the first converter substance (reference no. 30 in FIG. 1) was a YAG:Ce ceramic material with the composition $Y_{(3-x-y)}Gd_xAl_5O_{12}:Ce_y$, with x=0.3 and y=0.06.

The conversion element on Example II is CaS:Eu with 0.1% Europium.

The light delivery device furthermore comprises two sets of auxiliary LEDs (reference no. 40 in FIG. 1), which are also InGaN LEDs emitting at 450 nm. Each set of LEDs has a "strength" of 50% of the first LED.

FIG. 7 shows the spectra of the light delivery device with the first LED only ("LED"), with one set of auxiliary LEDs switched on ("Aux1") and with both sets of auxiliary LEDs switched on ("Aux2").

The data of FIG. 7 are listed in Table III:

TABLE III

| | LED | Aux 1 | Aux 2 |
|---|---|---|---|
| 380 | 0.002731 | 0.002811 | 0.002891 |
| 382 | 0.00246 | 0.00254 | 0.00262 |
| 384 | 0.002295 | 0.002375 | 0.002455 |
| 386 | 0.002183 | 0.002263 | 0.002343 |
| 388 | 0.0021 | 0.00218 | 0.00226 |
| 390 | 0.002063 | 0.002143 | 0.002223 |
| 392 | 0.001984 | 0.002064 | 0.002144 |
| 394 | 0.001932 | 0.002012 | 0.002092 |
| 396 | 0.001891 | 0.001971 | 0.002051 |
| 398 | 0.001885 | 0.001965 | 0.002045 |
| 400 | 0.001894 | 0.001974 | 0.002054 |
| 402 | 0.001904 | 0.001984 | 0.002064 |
| 404 | 0.001916 | 0.001996 | 0.002076 |
| 406 | 0.00201 | 0.00209 | 0.00217 |
| 408 | 0.002198 | 0.002278 | 0.002358 |
| 410 | 0.002487 | 0.002567 | 0.002647 |
| 412 | 0.00291 | 0.00299 | 0.00307 |
| 414 | 0.003532 | 0.003612 | 0.003692 |
| 416 | 0.004441 | 0.004521 | 0.004601 |
| 418 | 0.005643 | 0.005723 | 0.005803 |
| 420 | 0.007188 | 0.007268 | 0.007348 |
| 422 | 0.009126 | 0.009206 | 0.009286 |
| 424 | 0.011543 | 0.011623 | 0.011703 |
| 426 | 0.014461 | 0.014541 | 0.014621 |
| 428 | 0.017876 | 0.017956 | 0.018036 |
| 430 | 0.021857 | 0.021937 | 0.022017 |
| 432 | 0.026492 | 0.026572 | 0.026652 |
| 434 | 0.031853 | 0.031933 | 0.032013 |
| 436 | 0.037928 | 0.038008 | 0.038088 |
| 438 | 0.044757 | 0.044837 | 0.044917 |
| 440 | 0.052341 | 0.052421 | 0.052501 |
| 442 | 0.06054 | 0.06062 | 0.0607 |
| 444 | 0.069068 | 0.069148 | 0.069228 |
| 446 | 0.0776 | 0.07768 | 0.07776 |
| 448 | 0.085827 | 0.085907 | 0.085987 |
| 450 | 0.093335 | 0.093415 | 0.093495 |
| 452 | 0.099715 | 0.099795 | 0.099875 |
| 454 | 0.104735 | 0.104815 | 0.104895 |
| 456 | 0.108405 | 0.108485 | 0.108565 |
| 458 | 0.110776 | 0.110856 | 0.110936 |
| 460 | 0.111859 | 0.111939 | 0.112019 |
| 462 | 0.111729 | 0.111809 | 0.111889 |
| 464 | 0.110624 | 0.110704 | 0.110784 |

TABLE III-continued

| | LED | Aux 1 | Aux 2 |
|---|---|---|---|
| 466 | 0.10875 | 0.10883 | 0.10891 |
| 468 | 0.106153 | 0.106233 | 0.106313 |
| 470 | 0.102863 | 0.102943 | 0.103023 |
| 472 | 0.099002 | 0.099082 | 0.099162 |
| 474 | 0.094808 | 0.094888 | 0.094968 |
| 476 | 0.090407 | 0.090487 | 0.090567 |
| 478 | 0.085859 | 0.085939 | 0.086019 |
| 480 | 0.081277 | 0.081357 | 0.081437 |
| 482 | 0.076808 | 0.076888 | 0.076968 |
| 484 | 0.072592 | 0.072672 | 0.072752 |
| 486 | 0.068674 | 0.068754 | 0.068834 |
| 488 | 0.06512 | 0.0652 | 0.06528 |
| 490 | 0.062011 | 0.062091 | 0.062171 |
| 492 | 0.059401 | 0.059481 | 0.059561 |
| 494 | 0.057342 | 0.057422 | 0.057502 |
| 496 | 0.055892 | 0.055972 | 0.056052 |
| 498 | 0.055102 | 0.055182 | 0.055262 |
| 500 | 0.054976 | 0.055056 | 0.055136 |
| 502 | 0.055448 | 0.055528 | 0.055608 |
| 504 | 0.056473 | 0.056553 | 0.056633 |
| 506 | 0.057981 | 0.058061 | 0.058141 |
| 508 | 0.059874 | 0.059954 | 0.060034 |
| 510 | 0.06208 | 0.06216 | 0.06224 |
| 512 | 0.064504 | 0.064584 | 0.064664 |
| 514 | 0.067104 | 0.067184 | 0.067264 |
| 516 | 0.069813 | 0.069893 | 0.069973 |
| 518 | 0.072572 | 0.072652 | 0.072732 |
| 520 | 0.075336 | 0.075416 | 0.075496 |
| 522 | 0.078019 | 0.078099 | 0.078179 |
| 524 | 0.08058 | 0.08066 | 0.08074 |
| 526 | 0.082985 | 0.083065 | 0.083145 |
| 528 | 0.085209 | 0.085289 | 0.085369 |
| 530 | 0.087237 | 0.087317 | 0.087397 |
| 532 | 0.089072 | 0.089152 | 0.089232 |
| 534 | 0.090731 | 0.090811 | 0.090891 |
| 536 | 0.092226 | 0.092306 | 0.092386 |
| 538 | 0.093548 | 0.093628 | 0.093708 |
| 540 | 0.094726 | 0.094806 | 0.094886 |
| 542 | 0.09578 | 0.09586 | 0.09594 |
| 544 | 0.0967 | 0.09678 | 0.09686 |
| 546 | 0.097504 | 0.097584 | 0.097664 |
| 548 | 0.098204 | 0.098284 | 0.098364 |
| 550 | 0.098803 | 0.098883 | 0.098963 |
| 552 | 0.099295 | 0.099375 | 0.099455 |
| 554 | 0.099666 | 0.099746 | 0.099826 |
| 556 | 0.099941 | 0.100021 | 0.100101 |
| 558 | 0.10014 | 0.100253 | 0.100366 |
| 560 | 0.100248 | 0.100352 | 0.100457 |
| 562 | 0.100278 | 0.100419 | 0.10056 |
| 564 | 0.100233 | 0.10041 | 0.100586 |
| 566 | 0.10013 | 0.100255 | 0.10038 |
| 568 | 0.099938 | 0.100226 | 0.100514 |
| 570 | 0.099644 | 0.099935 | 0.100225 |
| 572 | 0.099263 | 0.099655 | 0.100047 |
| 574 | 0.09881 | 0.099252 | 0.099693 |
| 576 | 0.098291 | 0.098948 | 0.099605 |
| 578 | 0.097708 | 0.09838 | 0.099052 |
| 580 | 0.097084 | 0.098111 | 0.099137 |
| 582 | 0.096427 | 0.097766 | 0.099105 |
| 584 | 0.095733 | 0.097249 | 0.098765 |
| 586 | 0.094989 | 0.096655 | 0.098321 |
| 588 | 0.094207 | 0.096499 | 0.098791 |
| 590 | 0.093417 | 0.096078 | 0.098739 |
| 592 | 0.092576 | 0.096145 | 0.099715 |
| 594 | 0.091684 | 0.095957 | 0.100231 |
| 596 | 0.090785 | 0.095981 | 0.101177 |
| 598 | 0.089914 | 0.09634 | 0.102765 |
| 600 | 0.089023 | 0.097329 | 0.105635 |
| 602 | 0.088138 | 0.097263 | 0.106389 |
| 604 | 0.087334 | 0.097683 | 0.108031 |
| 606 | 0.086558 | 0.099057 | 0.111555 |
| 608 | 0.08584 | 0.101103 | 0.116365 |
| 610 | 0.085138 | 0.102026 | 0.118914 |
| 612 | 0.084485 | 0.104488 | 0.12449 |
| 614 | 0.083873 | 0.107333 | 0.130793 |
| 616 | 0.08323 | 0.109446 | 0.135663 |
| 618 | 0.082661 | 0.113232 | 0.143802 |
| 620 | 0.082144 | 0.116123 | 0.150101 |
| 622 | 0.081627 | 0.118431 | 0.155235 |
| 624 | 0.08123 | 0.122007 | 0.162784 |
| 626 | 0.080804 | 0.124579 | 0.168354 |
| 628 | 0.08048 | 0.128565 | 0.176649 |
| 630 | 0.080106 | 0.132753 | 0.1854 |
| 632 | 0.079787 | 0.135032 | 0.190277 |
| 634 | 0.079415 | 0.140028 | 0.200642 |
| 636 | 0.078916 | 0.141712 | 0.204508 |
| 638 | 0.078449 | 0.145427 | 0.212405 |
| 640 | 0.077836 | 0.146472 | 0.215107 |
| 642 | 0.077139 | 0.150875 | 0.224611 |
| 644 | 0.076284 | 0.150698 | 0.225112 |
| 646 | 0.075289 | 0.150925 | 0.226561 |
| 648 | 0.074195 | 0.152055 | 0.229916 |
| 650 | 0.072828 | 0.150963 | 0.229098 |
| 652 | 0.071378 | 0.149344 | 0.227309 |
| 654 | 0.069852 | 0.149852 | 0.229852 |
| 656 | 0.068139 | 0.145939 | 0.223738 |
| 658 | 0.066397 | 0.143834 | 0.221272 |
| 660 | 0.064552 | 0.138972 | 0.213393 |
| 662 | 0.062615 | 0.136383 | 0.210151 |
| 664 | 0.060556 | 0.133304 | 0.206053 |
| 666 | 0.0584 | 0.129308 | 0.200216 |
| 668 | 0.056123 | 0.125063 | 0.194003 |
| 670 | 0.053743 | 0.120684 | 0.187625 |
| 672 | 0.05133 | 0.113789 | 0.176248 |
| 674 | 0.049083 | 0.108819 | 0.168556 |
| 676 | 0.046732 | 0.103957 | 0.161182 |
| 678 | 0.044451 | 0.097638 | 0.150824 |
| 680 | 0.042273 | 0.091529 | 0.140785 |
| 682 | 0.040124 | 0.086984 | 0.133844 |
| 684 | 0.038025 | 0.083943 | 0.129862 |
| 686 | 0.035843 | 0.076383 | 0.116923 |
| 688 | 0.033855 | 0.073202 | 0.112548 |
| 690 | 0.031863 | 0.068753 | 0.105643 |
| 692 | 0.029922 | 0.062992 | 0.096063 |
| 694 | 0.028121 | 0.059684 | 0.091248 |
| 696 | 0.026411 | 0.055107 | 0.083803 |
| 698 | 0.024817 | 0.0518 | 0.078783 |
| 700 | 0.023267 | 0.04813 | 0.072993 |
| 702 | 0.021803 | 0.044705 | 0.067606 |
| 704 | 0.020463 | 0.041375 | 0.062287 |
| 706 | 0.019186 | 0.038765 | 0.058343 |
| 708 | 0.017968 | 0.035719 | 0.05347 |
| 710 | 0.016772 | 0.033093 | 0.049414 |
| 712 | 0.015685 | 0.030275 | 0.044866 |
| 714 | 0.014667 | 0.029027 | 0.043387 |
| 716 | 0.013678 | 0.026584 | 0.039491 |
| 718 | 0.012728 | 0.02487 | 0.037012 |
| 720 | 0.011838 | 0.021897 | 0.031956 |
| 722 | 0.011087 | 0.020362 | 0.029638 |
| 724 | 0.010336 | 0.018908 | 0.02748 |
| 726 | 0.009658 | 0.017608 | 0.025558 |
| 728 | 0.00902 | 0.015997 | 0.022974 |
| 730 | 0.008502 | 0.014717 | 0.020931 |
| 732 | 0.007991 | 0.013938 | 0.019885 |
| 734 | 0.007478 | 0.012436 | 0.017395 |
| 736 | 0.007028 | 0.012045 | 0.017063 |
| 738 | 0.00659 | 0.010689 | 0.014789 |
| 740 | 0.006218 | 0.010233 | 0.014248 |
| 742 | 0.005813 | 0.009442 | 0.013072 |
| 744 | 0.005459 | 0.008447 | 0.011434 |
| 746 | 0.005142 | 0.007815 | 0.010488 |
| 748 | 0.004859 | 0.007119 | 0.009379 |
| 750 | 0.004616 | 0.007121 | 0.009627 |
| 752 | 0.004355 | 0.006159 | 0.007964 |
| 754 | 0.004116 | 0.006123 | 0.008129 |
| 756 | 0.003899 | 0.005788 | 0.007677 |
| 758 | 0.003704 | 0.005228 | 0.006752 |
| 760 | 0.003509 | 0.00523 | 0.006952 |
| 762 | 0.00331 | 0.004353 | 0.005396 |
| 764 | 0.003101 | 0.004161 | 0.005221 |
| 766 | 0.002911 | 0.003969 | 0.005027 |
| 768 | 0.002731 | 0.003769 | 0.004806 |
| 770 | 0.002567 | 0.003607 | 0.004647 |
| 772 | 0.002475 | 0.003363 | 0.004251 |
| 774 | 0.002384 | 0.003092 | 0.0038 |
| 776 | 0.002342 | 0.002933 | 0.003525 |

TABLE III-continued

|  | LED | Aux 1 | Aux 2 |
|---|---|---|---|
| 778 | 0.002329 | 0.002724 | 0.003118 |
| 780 | 0.002339 | 0.002902 | 0.003465 |

Further data of Example II are given in Table IV:

TABLE IV

|  | LED | Aux1 | Aux2 |
|---|---|---|---|
| CCT [K] | 4881 | 3895 | 3180 |
| Ra | 88 | 93 | 83 |
| uv | 0.004 | 0.008 | 0.016 |
| x | 0.3494 | 0.3788 | 0.4035 |
| y | 0.3632 | 0.3579 | 0.3535 |
| LE [lm/W] | 297 | 254 | 226 |
| R1 | 86.3 | 92 | 78.4 |
| R2 | 94.1 | 94.2 | 85 |
| R3 | 96.4 | 96.1 | 97 |
| R4 | 80.1 | 97.2 | 85.9 |
| R5 | 83.8 | 93.4 | 79.5 |
| R6 | 88.3 | 94.3 | 83 |
| R7 | 90.9 | 96.4 | 92.4 |
| R8 | 80.2 | 84.1 | 65 |
| R9 | 50.1 | 58.2 | 16.2 |
| R10 | 82.5 | 92.9 | 73 |
| R11 | 76.5 | 97.7 | 84.7 |
| R12 | 62.9 | 79.4 | 66.8 |
| R13 | 88.6 | 92.1 | 78.6 |
| R14 | 97.9 | 96.4 | 96.6 |

It can be clearly seen that a shift of the color temperature over approx. 1700K is possible without any deterioration in the lighting properties, such as the Ra of the light delivery device.

In both examples it is possible to simply "add" red light, i.e. the spectra in the wavelength range of 380 to 580 nm are more or less identical for "LED", "Aux1" as well as "Aux2".

It should be noted that in both examples the light flux even increases by switching on the LED groups Aux1 and Aux2. If a constant flux is required, the first LED may be dimmed when the Aux1 and Aux2 LEDs are switched on. In this case the color temperature will be decreased even further with the full power of the Aux1 and Aux2 LEDs added. It is evident that the light flux of all LEDs can be tuned to any desired value between the maximum power applicable to the LED package and zero. Power can be modified either by increasing and decreasing the DC voltage and current or by application of fast current and voltage pulses at a frequency>10 Hz and modifying the ratio of the on and off-time of the power.

The particular combinations of elements and features in the above detailed embodiments are exemplary only; the interchanging and substitution of these teachings with other teachings in this patent application and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the above description is by way of example only, and is not intended to be limiting. The invention's scope is defined in the following claims and the equivalents thereto. Furthermore, reference signs used in the description and claims do not limit the scope of the invention as claimed.

The invention claimed is:

1. A light delivery device, comprising:
    a wavelength conversion element having a first input surface area, a second input surface area, and an output surface area, the second input surface area being larger than and non-planar with the first input surface area,
    a first LED source configured to emit first light having a first peak emission wavelength toward the first input surface area of the wavelength conversion element;
    a second LED source configured to emit second light having a second peak emission wavelength different from the first peak emission wavelength toward the second input surface area of the wavelength conversion element; and
    wherein the second LED source is controlled such that an intensity of the second light adjusts a color temperature of converted light emitted from the output surface area of the wavelength conversion element; and
    wherein the converted light is converted within the at least one conversion element.

2. The light delivery device of claim 1, wherein a combined light entry surface area of the first and second input surface areas is substantially larger than the output surface area.

3. The light delivery device of claim 1, wherein:
    the wavelength conversion element has a rectangular profile,
    the first input surface area and the output surface area are on opposing sides of the rectangular profile, and
    the second input surface area is substantially orthogonal to the first input surface area and the output surface area.

4. The light delivery device of claim 1, wherein the second LED source includes a plurality of light sources, and controlling the intensity of the second light source includes enabling a select number of the plurality of light sources.

5. The light delivery device of claim 1, wherein the wavelength conversion element is substantially cylindrical, and the second LED source comprise a plurality of light sources arranged in a ring that is coaxial with the wavelength conversion element.

6. A method comprising:
    providing a wavelength conversion element having a first input surface area, a second input surface area, and an output surface area, the second input surface area being larger than and non-planar with the first input surface area,
    providing first light, having a first peak emission wavelength, from a first LED source toward the first input surface area of the wavelength conversion element;
    providing second light, having a second peak emission wavelength different from the first peak emission wavelength, from a second LED source toward the second input surface area of the wavelength conversion element; and
    controlling an intensity of the second light to adjust a color temperature of converted light emitted from the output surface area of the wavelength conversion element;
    wherein the converted light is converted within the at least one conversion element.

7. The method of claim 6, wherein:
    the wavelength conversion element has a rectangular profile,
    the first input surface area and the output surface area are on opposing sides of the rectangular profile, and
    the second input surface area is substantially orthogonal to the first input surface area and the output surface area.

8. The method of claim 6, wherein the second light source includes a plurality of light sources, and controlling the intensity of the second light source includes enabling a select number of the plurality of light sources.

9. The method of claim 6, including maintaining a substantially constant quantity of light flux of the emitted light independent of the adjusted color temperature of the emitted light from the wavelength conversion element.

10. The method of claim 6, wherein increasing the intensity of the second light reduces the color temperature of the emitted light from the wavelength conversion element.

11. The method of claim 6, wherein increasing the intensity of the second light adds red light to a spectrum of the emitted light from the wavelength conversion element.

12. The method of claim 6, wherein controlling the intensity of the second light to adjust the color temperature of emitted light from the wavelength conversion element provides an adjustment of the color temperature of emitted light by at least 1600 K.

13. The method of claim 6, including controlling an intensity of the first light to further adjust the color temperature of emitted light from the wavelength conversion element.

14. The method of claim 6, wherein the wavelength conversion element is substantially cylindrical, and the second light source comprise a plurality of light sources arranged in a ring that is coaxial with the wavelength conversion element.

15. The method of claim 6, wherein the second input surface area is substantially larger than the first input surface area.

16. The method of claim 15, wherein a combined light entry surface area of the first and second input surface areas is substantially larger than the output surface area.

* * * * *